(12) United States Patent
Timm et al.

(10) Patent No.: US 8,906,064 B2
(45) Date of Patent: Dec. 9, 2014

(54) INTERSPINOUS PROCESS DEVICE AND METHOD

(71) Applicants: Jens Peter Timm, Carlsbad, CA (US); Danielle Richterkessing, Carlsbad, CA (US); Jared Arambula, Carlsbad, CA (US)

(72) Inventors: Jens Peter Timm, Carlsbad, CA (US); Danielle Richterkessing, Carlsbad, CA (US); Jared Arambula, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 13/867,811

(22) Filed: Apr. 22, 2013

(65) Prior Publication Data

US 2013/0304125 A1 Nov. 14, 2013

Related U.S. Application Data

(60) Provisional application No. 61/636,953, filed on Apr. 23, 2012.

(51) Int. Cl.
*A61F 2/44* (2006.01)
*A61B 17/70* (2006.01)

(52) U.S. Cl.
CPC ................................. *A61B 17/7068* (2013.01)

USPC ........................................ 606/248; 623/17.11

(58) Field of Classification Search
USPC ..................... 606/246–249; 623/17.11–17.16
See application file for complete search history.

(56) References Cited

U.S. PATENT DOCUMENTS

| | | | |
|---|---|---|---|
| 6,183,471 B1 * | 2/2001 | Zucherman et al. | 606/249 |
| 7,048,736 B2 | 5/2006 | Robinson | |
| 2007/0093824 A1 * | 4/2007 | Hestad et al. | 606/61 |
| 2008/0183211 A1 | 7/2008 | Lamborne et al. | |
| 2010/0036419 A1 | 2/2010 | Patel et al. | |
| 2010/0152780 A1 | 6/2010 | Stevenson et al. | |
| 2011/0137403 A1 | 6/2011 | Rasmussen et al. | |
| 2011/0160772 A1 * | 6/2011 | Arcenio et al. | 606/248 |

* cited by examiner

*Primary Examiner* — Mary Hoffman
*Assistant Examiner* — Tara Carter
(74) *Attorney, Agent, or Firm* — Michael J. Loi

(57) ABSTRACT

A system for surgically coupling the spinous processes includes a first plate, a second plate, a pair of semi-rigid guide members, and a coupler. The first plate engages with a first lateral side of the spinous processes. The pair of semi-rigid guide members attaches to the first plate for inserting the first plate between the spinous processes. The second plate includes a pair of apertures that slide over the pair of semi-rigid guide members engage a second lateral side of the spinous processes. The coupler couples the first plate and the second plate together.

13 Claims, 5 Drawing Sheets

INTERSPINOUS PROCESS DEVICE AND METHOD

FIELD

The present disclosure generally relates to the field of spinal orthopedics, and more particularly to an interspinous process device and method.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae. When the vertebrae are articulated with each other, the bodies form a strong pillar for the support of the head and trunk, and the vertebral foramina constitute a canal for the protection of the medulla spinalis (spinal cord). In between every pair of vertebrae are two apertures, the intervertebral foramina, one on either side, for the transmission of the spinal nerves and vessels.

A typical vertebra consists of two essential parts: an anterior (front) segment, which is the vertebral body; and a posterior part—the vertebral (neural) arch—which encloses the vertebral foramen. The vertebral arch is formed by a pair of pedicles and a pair of laminae, and supports seven processes, four articular, two transverse, and one spinous, the latter also being known as the neural spine.

Two transverse processes and one spinous process are posterior to (behind) the vertebral body. The spinous process comes out the back, one transverse process comes out the left, and one on the right. The spinous process of a vertebra is directed backward and downward from the junction of the laminae (in humans), and serves for the attachment of muscles and ligaments. The spinous processes of the cervical and lumbar regions can be felt through the skin. Superior and inferior articular facets on each vertebra act to restrict the range of movement possible. These facets are joined by a thin portion of the neural arch called the pars interarticularis.

The correct curvature is obtained by manipulating the vertebrae into their proper position and securing that position with various devices. For example, screws and rods may be implanted into the pedicles and posterior portions of the vertebrae along with interbody spacers and cages between the vertebrae. Plates may be implanted on anterior and lateral portions of the vertebrae. Another option includes coupling facet joints. Yet another approach includes devices for attachment to the spinous processes of the vertebrae.

Current interspinous process fusion and non-fusion devices require a direct mid-line incision large enough to expose the affected interspinous space. Additionally, typical interspinous process devices and methods require sacrificing the supraspinous ligament, a strong fibrous cord, which connects together the apices of the spinous processes from the seventh cervical vertebra to the sacrum. The device and method of the present application includes an interspinous process approach for fusion and non-fusion surgeries that accomplishes the same placement goals as the mid-line approach. The device and method decreases the incisions size and the amount of tissue disturbed by the procedure.

SUMMARY

A system for surgically coupling the spinous processes includes a first plate, a second plate, a pair of semi-rigid guide members, and a coupler. The first plate engages with a first lateral side of the spinous processes. The pair of semi-rigid guide members attaches to the first plate for inserting the first plate between the spinous processes. The second plate includes a pair of apertures that slide over the pair of semi-rigid guide members engage a second lateral side of the spinous processes. The coupler couples the first plate and the second plate together.

A system for surgically coupling a first spinous process with a second spinous process includes a first plate, a second plate, a pair of guide members, and a coupler. The first plate includes an opening extending from a first lateral surface to a first medial surface. The second plate includes a pair of apertures extending from a second lateral surface to a second medial surface. The pair of guide members includes flexible portions that attach to the first plate and elongate portions received by the pair of apertures for guiding the second plate towards the first plate. The coupler is disposed between the pair of guide members and engages the opening to couple the first plate with the second plate.

In other features, the system includes a lock member that engages a notch of the opening. The system includes a plurality of vertebral engagement features on the first and second medial surfaces. The system includes a slot in the coupler for receiving bone-fusion material. The system includes a set screw for locking the second plate to the first plate. The system includes a tapered entry portion of the coupler for advancement through tissue and insertion into the opening. The guide members include one of rods, semi-flexible cables, semi-rigid cables, and living hinges. The system includes a first shaped region on an upper section of the plates that mates with a second shaped region on a lower section of the plates.

In still other features, the system includes a third plate, a fourth plate, a second pair of guide members, and a second coupler. The third plate includes a second opening extending from a third lateral surface to a third medial surface. The fourth plate includes a second pair of apertures extending from a fourth lateral surface to a fourth medial surface. The second pair of guide members includes flexible portions that attach to the third plate and elongate portions received by the second pair of apertures for guiding the fourth plate towards the third plate. The second coupler is disposed between the second pair of guide members and engages the second opening to couple the third plate with the fourth plate. The first and second plates include a first shaped region on an upper section that mates with a second shaped region on a lower section of the third and fourth plates.

A method for surgically coupling spinous processes includes the steps of inserting a first plate between a first and second spinous process and beneath a supraspinous ligament connecting the first and second spinous processes using a pair of guide members; engaging the first plate with first lateral sides of the first and second spinous processes; sliding a second plate over the pair of guide members; advancing the second plate to engage second lateral sides of the first and second spinous processes; and inserting a coupler through an opening of the first plate to rigidly couple the first and second plates.

In other features, the method includes attaching a pair of retention members on the pair of guide members on a lateral side of the second plate to maintain tension on the pair of guide members. The method includes cutting a length from each of the guide members. The pair of guide members comprise one of rods, semi-flexible cables, semi-rigid cables, and living hinges.

DETAILED DESCRIPTION

Figure 1:
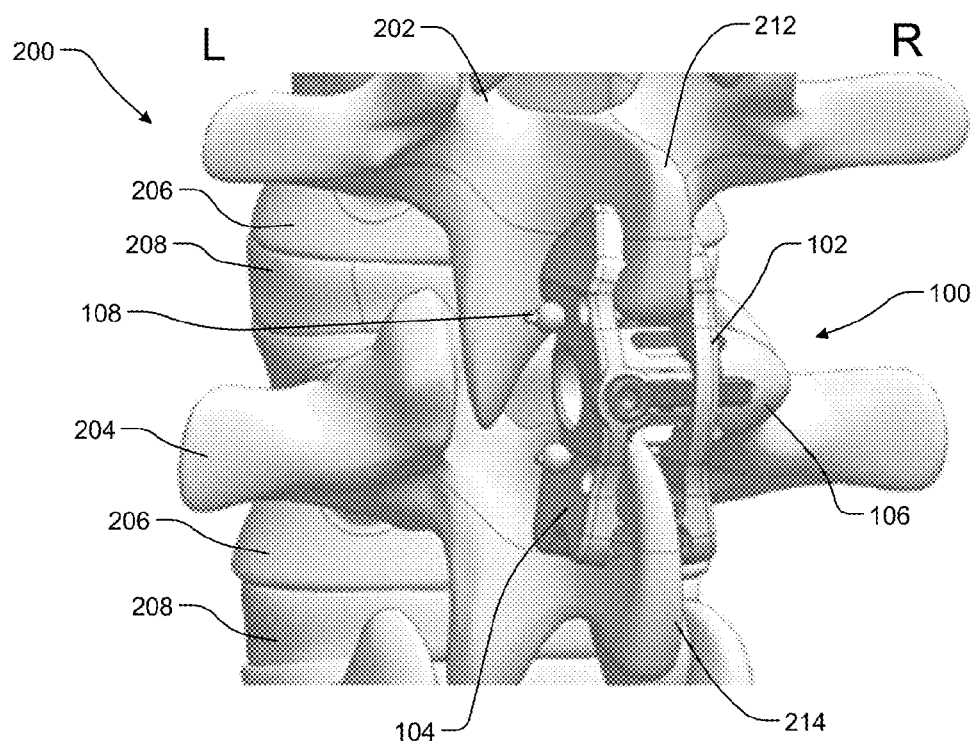
FIG. 1 is a perspective view of an exemplary device for surgically coupling spinous processes of vertebrae according to the principles of the present disclosure.
Figure 2:
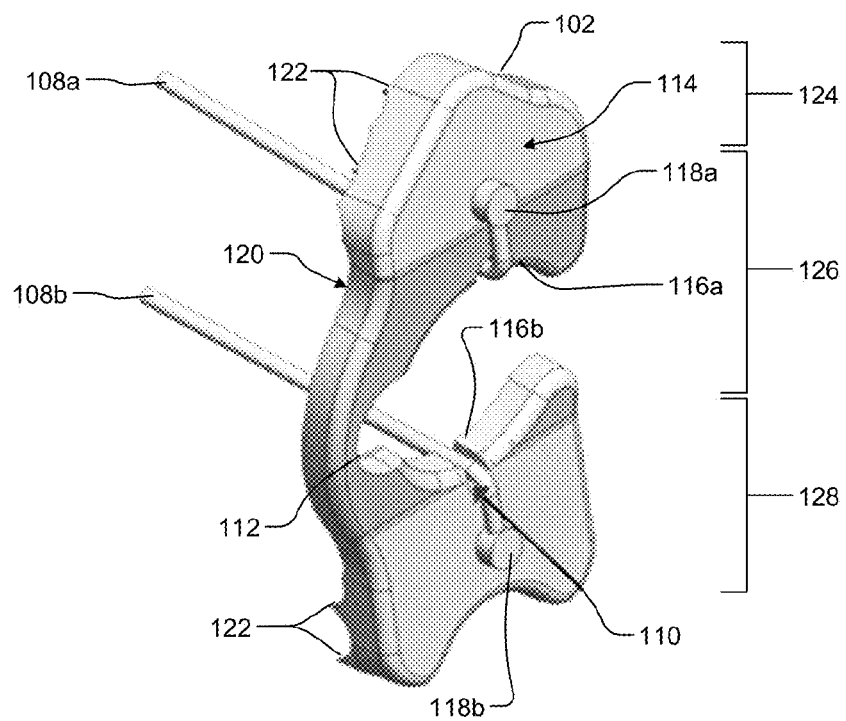
FIG. 2 is a perspective view of a portion of the device of FIG. 1 according to the principles of the present disclosure.
Figure 3:
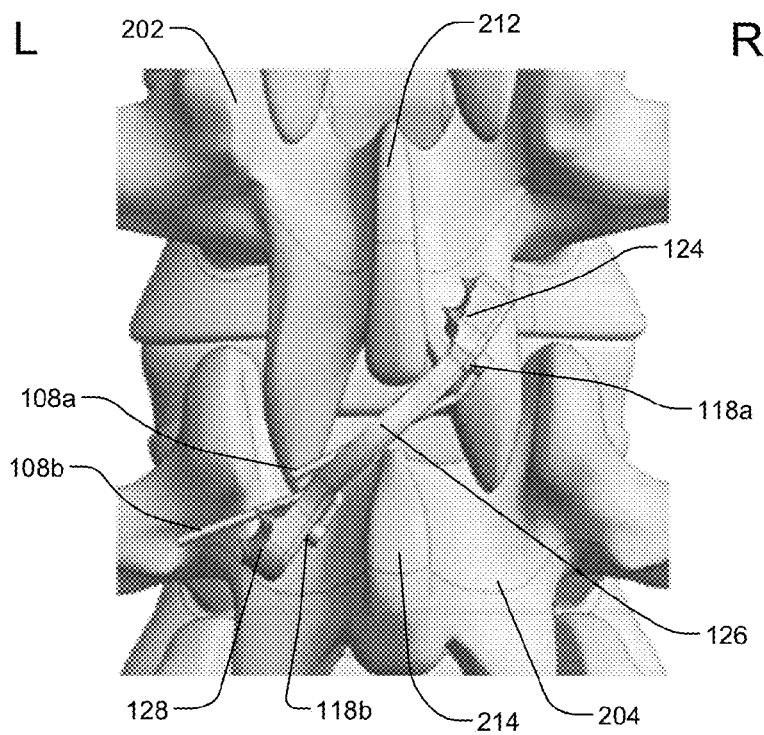
FIGS. 3-6 illustrate steps of a method for inserting the portion of the device of FIG. 2 and positioning the portion relative to the spinous processes according to the principles of the present disclosure.
Figure 4:
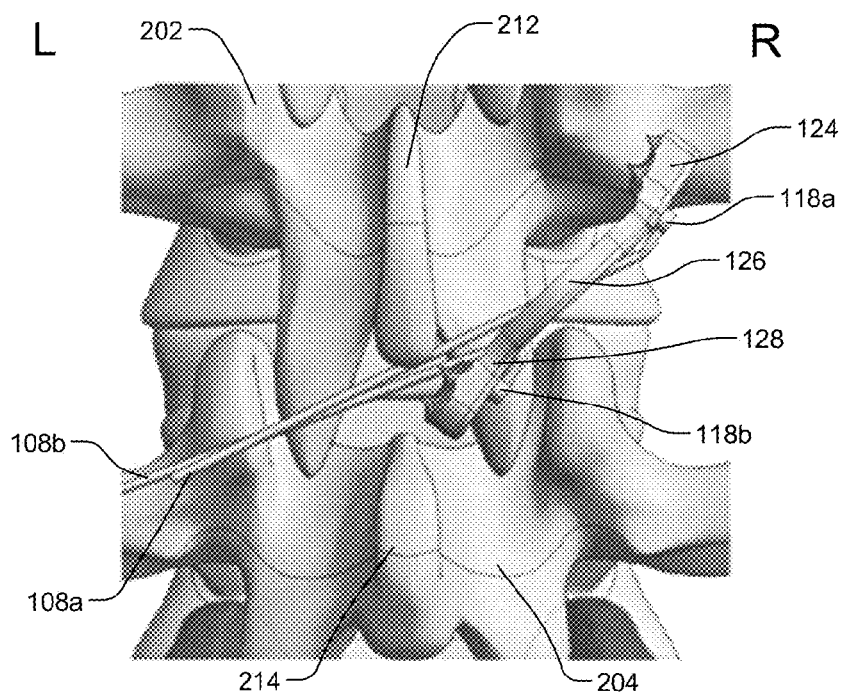

The exemplary device and method illustrated in FIGS. 1-8 reduces patient recovery time, preserves anatomy associated with biomechanical stability, and delivers a true minimally invasive system to the interspinous process space. The device may include a plate/distraction-cylinder component and a free plate component to which wire cables are attached. Two cables are attached to the exterior side of the free plate and are wrapped through the central hole so the cables are contained within the small recess features along the central hole and the ends are facing the inside of the plate as shown in FIG. 2. An insertion instrument attaches to the free plate along the inside wall of the central hole and the cables are placed along the instrument so they are not obstructing the work space. The instrument inserts the free plate at a diagonal through the interspinous space until the inferior edge clears the inferior spinous process as shown in FIGS. 3-4.

Figure 5:
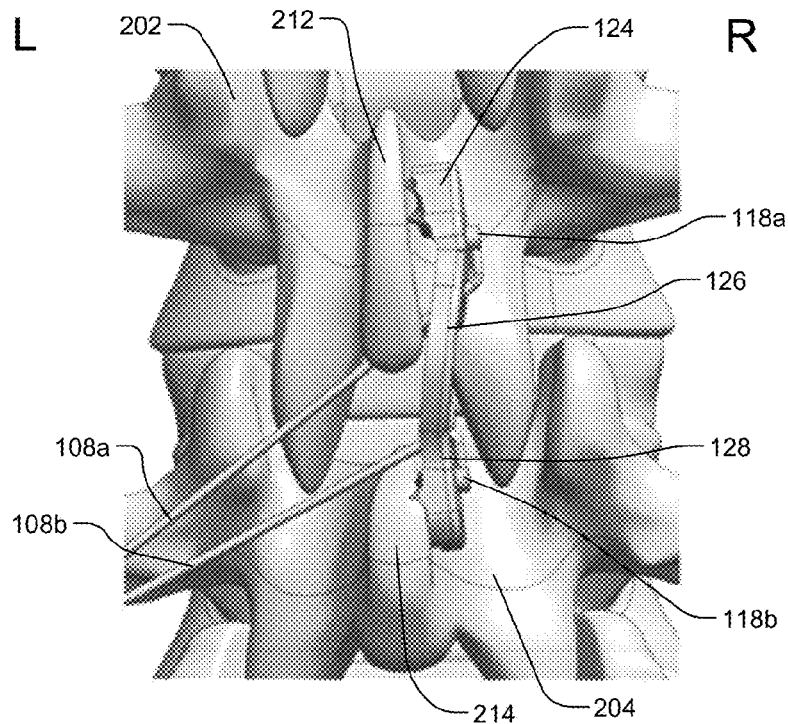
Figure 6:
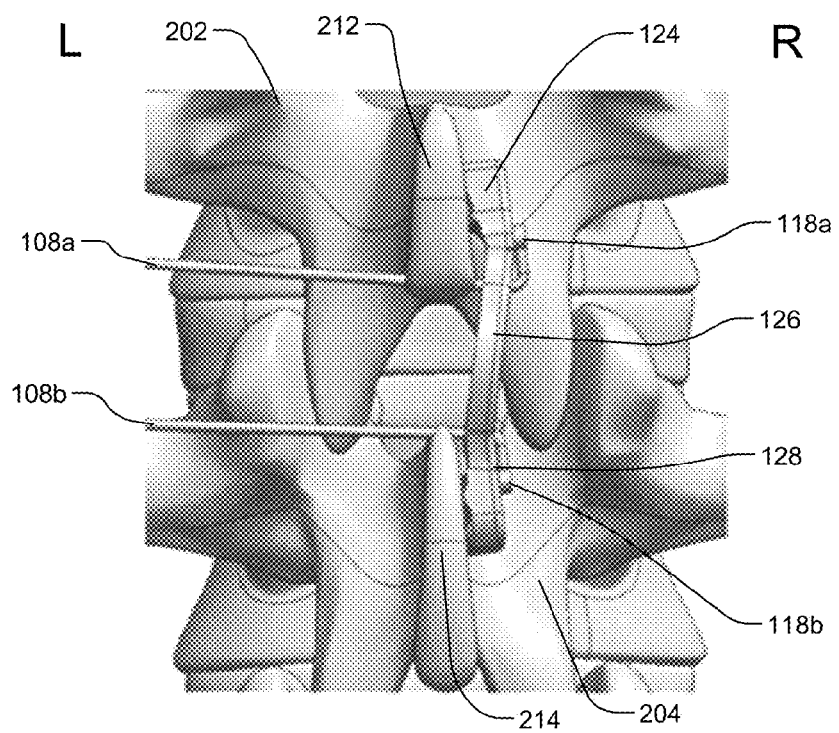
Figure 7:
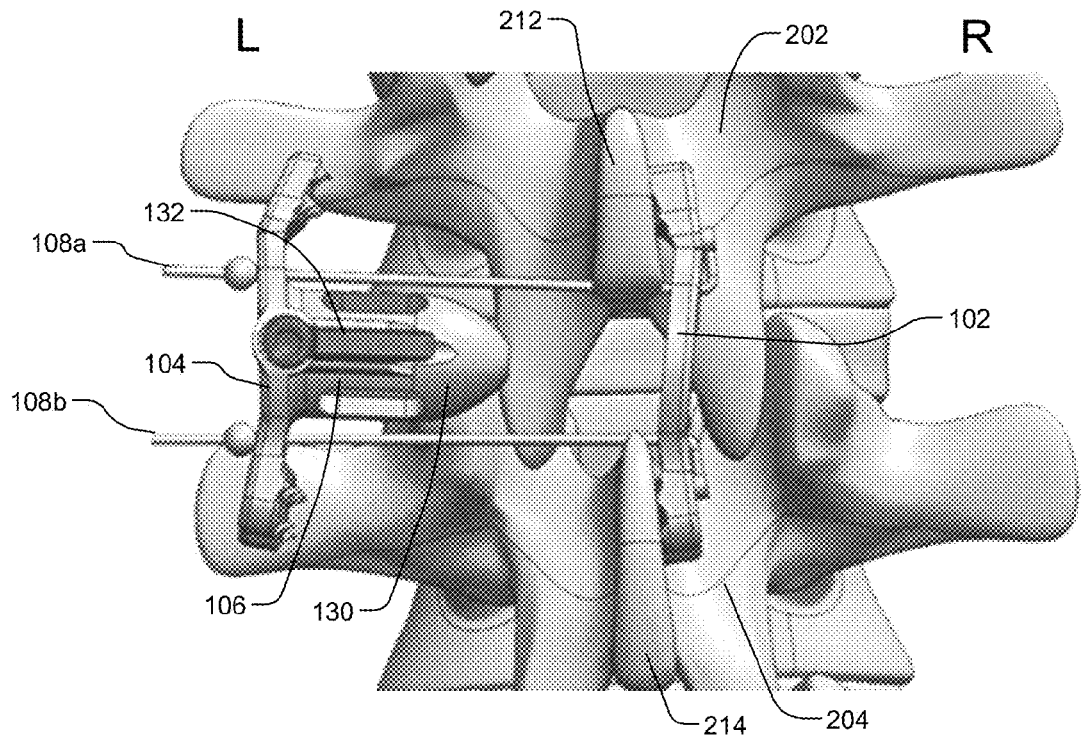
FIGS. 7 and 8 illustrate additional steps of the method for inserting additional portions of the device of FIG. 1 and positioning the additional portions relative to the spinous processes according to the principles of the present disclosure.
Figure 8:
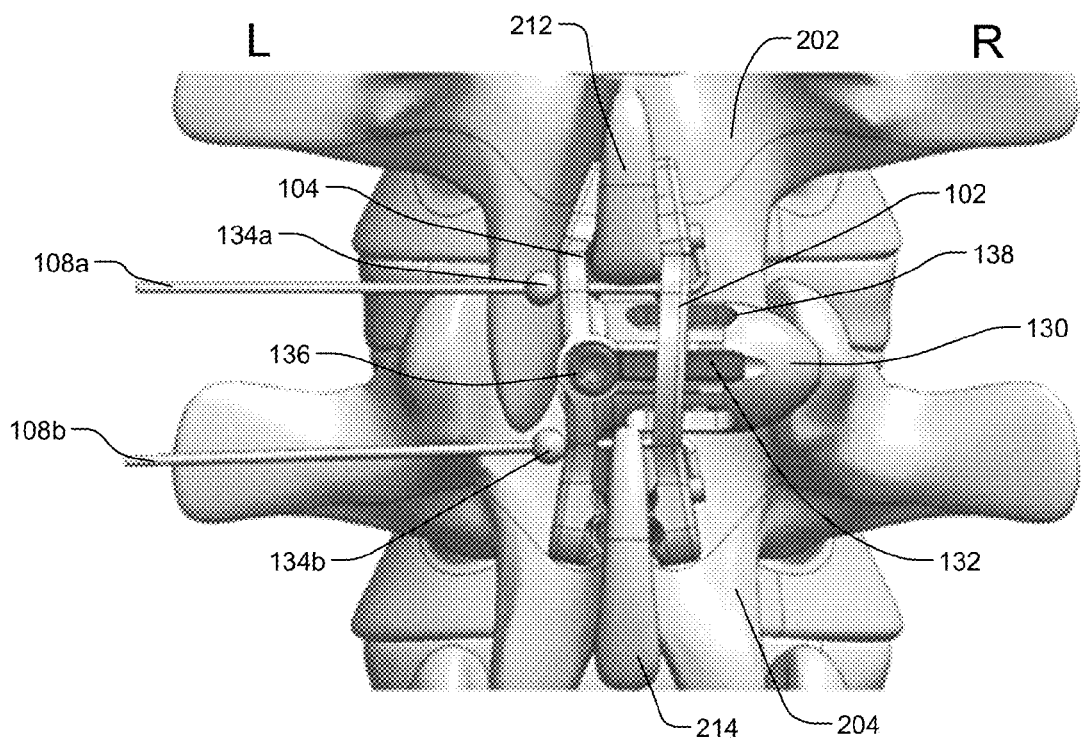

The instrument is released from the plate and the superior cable is pulled to position the plate parallel to the spinous processes as shown in FIG. 5. Then, the cables are manipulated to position the plate's central hole in line with the interspinous space as shown in FIG. 6. Next the superior cable is threaded through the superior hole on the plate/distraction-cylinder component and the inferior cable is threaded through the inferior hole on the same component as shown in FIG. 7. This allows the cylinder on the plate/distraction-cylinder component to align with the central hole on the free plate component. Once properly positioned, the device is compressed, crimping beads are used to lock the assembly in position, and all excess cable is trimmed as shown in FIGS. 1 and 8.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Referring now to FIG. 1, an exemplary interspinous process device 100 may be inserted between spinous processes of vertebrae of a spinal column 200. The spinal column 200 may include a first vertebra 202 and an adjacent second vertebra 204. The vertebrae may be any of cervical, thoracic, and lumbar vertebrae. In the present example, the vertebrae include thoracic vertebrae. The vertebrae may include other features such as bodies 206 separated by discs 208. Each of the vertebrae includes a spinous process. For example, the first vertebra 202 includes a first spinous process 212 and the second vertebra 204 includes a second spinous process 214. The device 100 may be used to secure the first vertebra 202 and the second vertebra 204 by attaching to the first spinous process 212 and the second spinous process 214.

The device 100 may include at least the components in the present example and method. The device 100 may include a first plate 102, a second plate 104, a coupler 106, and one or more guide members 108. The first plate 102 and the second plate 104 may comprise one or more biocompatible materials with sufficient strength to apply forces to the spinous processes for rigid or semi-rigid fixation of the vertebrae. For example, the material may comprise various types of titanium and titanium allows. The first plate 102 may engage first lateral sides of the spinous processes 212 and 214 and the second plate 104 may engage second lateral sides of the spinous processes 214. For example, the first lateral side may correspond to the right side of the patient and the second lateral side may correspond to the left side of the patient as indicated by the R and L in FIG. 1. The coupler 106 may be integral with one of the plates or independent and functions to rigidly secure the first plate 102 and the second plate 104 upon successful implantation. The guide member 108 may comprise any of a variety of flexible and semi-rigid materials and include components for both flexion and rigidity. For example, the guide member 108 may include a guide cable, a guide rod, or a combination of components. The guide member 108 may be capable of applying both tensile force (pulling) and compressive force (pushing) to maneuver the first plate 102 as describe herein.

Referring now to FIG. 2, the first plate 102 and a pair of cables 108 including a first cable 108a and a second cable 108b are shown. The first plate 102 may include a coupler opening 110 for receiving the coupler 106. The coupler opening 110 may be disposed generally centrally within the first plate 102. The coupler opening 110 may include one or more tracks, guide portions, or notches 112 for engaging and locking with mating features of the coupler 106. The cables 108 may attach to a lateral side 114 of the first plate 102. For example, the first cable 108a may extend through the coupler opening 110 in a first groove 116a and wrap around a portion of the first plate 102 to pivotally couple at a first pin 118a. The second cable 108b may extend through the coupler opening 110 in a second groove 116b and wrap around another portion of the first plate 102 to pivotally couple at a second pin 118b. In other examples, the cables 108 may pivotally couple to the opposite medial side 120 of the first plate 102. The medial side 120 may further include one or more vertebral engagement features 122, such as spikes, claws, ridges, beads, and the like, for engaging the spinous processes of the vertebrae. The engagement features 122 may pierce the spinous process to provide a rigid construct as disclosed herein.

The first plate 102 may include an upper section 124, a middle section 126, and a lower section 128. The upper section 124 may include the first pin 118a. The middle section 126 may include the coupler opening 110. The lower section 128 may include the second pin 118b. The upper section 124 may lie in a first plane substantially parallel to the anatomical sagittal plane. The lower section 128 may lie in a second plane substantially parallel to the anatomical sagittal plane. The middle section 126 may lie in a third plane that intersects the first and second planes. In one example, the upper section 124 and the lower section 128 may be parallel with the middle section 126 at an angle therebetween. Thus the first plate 102 may include bends between the various sections that aid with insertion as described herein. The first plate 102 may include a generally "S" shaped curvature from the upper section 124 to the lower section 128.

FIGS. 3-8 illustrate additional features of the device 100 as well as a method of inserting a device, such as device 100, for fixation of the spinous processes. In FIG. 3, the present exemplary device 100 may be inserted through a series of steps beginning with the first plate 102. The cables 108a and 108b may be used to direct the upper section 124 through the narrow space between the first spinous process 212 and the second spinous process 214. The cables 108 may articulate about the pins 118. The cables 108 may include substantially rigid properties when compressed and flexible properties in flexion. Alternately, the cables 108 may include rigid portions such as rods and flexible portions such as living hinges, coils, and the like. Thus, the first cable 108a may bend as it guides the upper section 124 between the first and second spinous processes 212 and 214. The first cable 108a may be in compression as it guides the upper section 124. The second cable 108b may also bend as it guides the lower section 128. The second cable 108b may be in tension as it guides the lower section 128.

Continuing with FIG. 4, the first and second cables 108a and 108b may advance the entire first plate 102 past the first and second spinous processes 212 and 214 and onto the right side of the spine 200. The first cable 108a may pull the upper section 124 while the second cable 108b may push the lower section 128. The cables 108 may be used to maneuver the first plate 102 within the narrow confines of the posterior portion of the vertebrae including the pedicles, articular processes, and transverse processes. In FIG. 5, the first and second cables 108a and 108b may pull the first plate 102 towards the spinous processes 212 and 214. Both the first and second cables 108a and 108b may be in tension. Due to the at least partially flexible features, the cables 108 may wrap around the spinous processes where other typical instruments cannot. The cables 108 may also pull the engagement features 122 of the plate 102 into contact with the spinous processes 212 and 214. These teeth and/or spikes may cut into the spinous processes as illustrated in FIG. 6.

Referring now to FIG. 7, the first plate 102 has been at least provisionally secured using the cables 108 and engagement features 122. The second plate 104 and coupler 106 may subsequently be inserted along the cables 108. For example, the second plate 104 and coupler 106 may be integrated. In other examples, the second plate 104 may be substantially a mirror image of the first plate 102. For example, the second plate 104 may include a second set of grooves 116 within its similar coupler opening 110, as in the first plate 102. Thus, grooves 116a and 116b may slide along the cables 108a and 108b respectively as the second plate 104 advances towards the first plate 102. The coupler 106 may include a tapered or conical-shaped entry portion 130 for advancement through various tissues surrounding the vertebrae 202 and 204.

As the second plate 104 and coupler 106 advance towards the first plate 102, as shown in FIG. 8, the entry portion 130 enters the coupler opening 110. The coupler 106 may include a locking member 132, such as a clip or other feature, that mates with the notch 112 in the coupler opening 110 of the first plate 102. The locking member 132 may be slide freely within the notch 112 as the second plate 104 is compressed against the first and second spinous processes 212 and 214. Retention members 134 may retain the first and second plate 102 and 104 in compression as the cables 108 apply tension to the first plate 102. For example, retention members 134a and 134b, which may include clips, caps, nuts, and the like, may engage the cables 108a and 108b near the second plate 104.

A lock screw 136 may secure the locking member 132 within the notch 112 of the coupler opening 110. The lock screw 136 may apply compressive force to retain the coupler 106 within the coupler opening 110. Referring back to FIG. 1, the cables 108a and 108b may be cut close to the retention members 134. The remaining portions of the cables 108a/108b between the pivots 118a/118b and the retention members 134a/134b may maintain tension to pull the first plate 102 and second plate 104 together. The coupler 106 may also apply compression forces to hold the plates 102 and 104 together. Slots 138 in the coupler 106 may provide passageways for bone material during fusion procedures.

Figure 9:
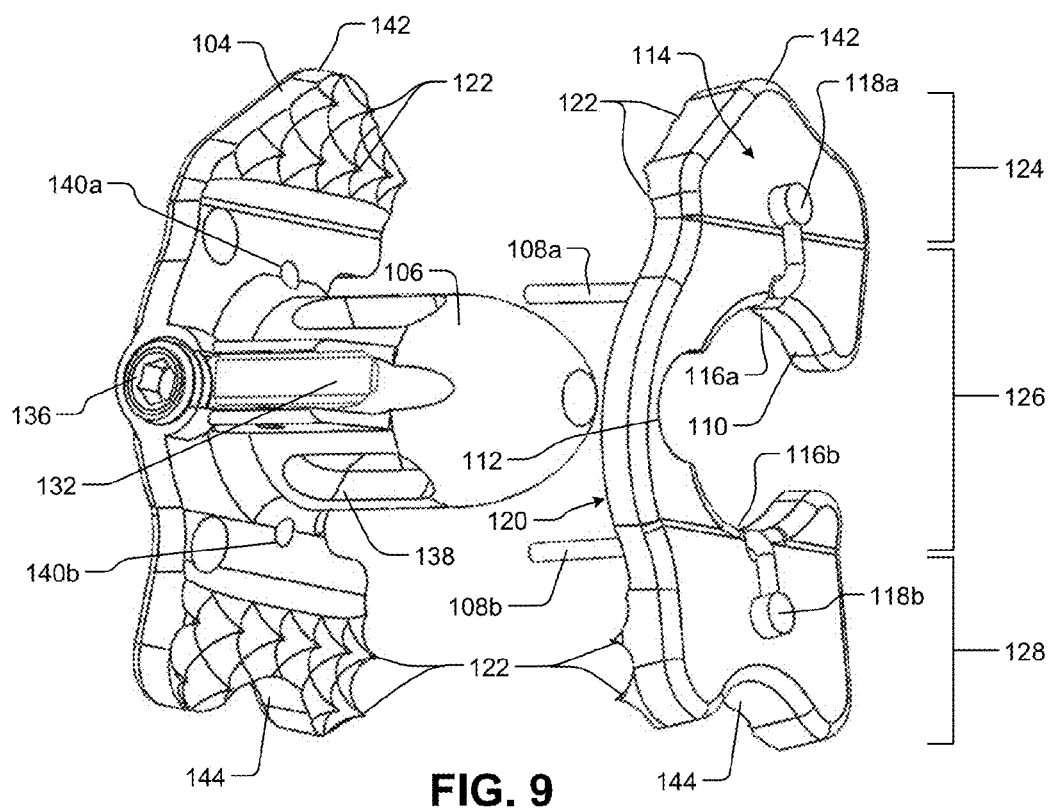
FIGS. 9 and 10 are perspective views of the device in a uncoupled and coupled configurations according to the principles of the present disclosure.
Figure 10:
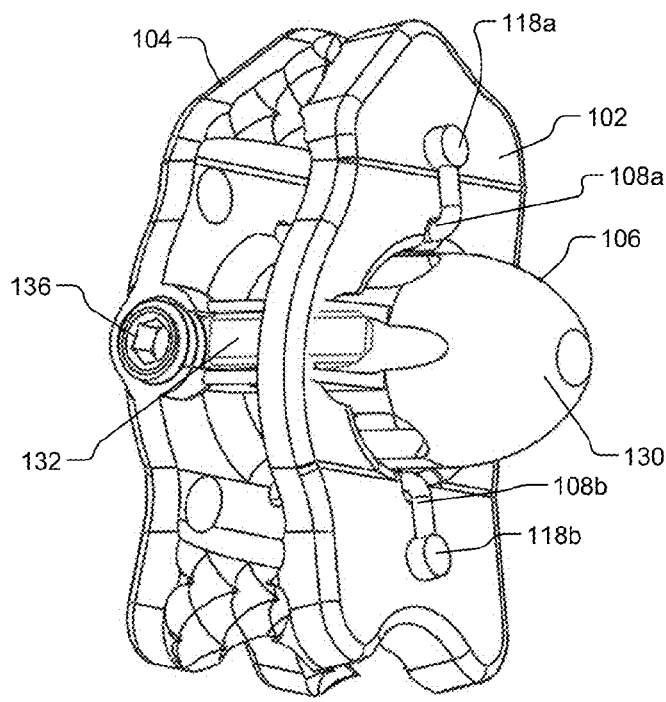

Referring now to FIGS. 9-10, perspective views of the device 100 illustrate coupling of the first plate 102 and second plate 104 via coupler 106 with guide members 108 (shown truncated in FIG. 9.) As can be seen, the second plate 104 and coupler 106 may slide over the guide member 108a and 108b via corresponding apertures 140a and 140b extending through the second plate 104. For example, upon insertion of the first plate 102 as shown in FIGS. 5 and 6, the second plate 104 may be positioned such that the apertures 140a and 140b align with the guide member 108a and 108b respectively. Then the second plate 104 may be guided towards the left side of the spinous processes 212 and 214. Because the apertures 140 and guide members 108 are aligned, the coupler 106 may align with the opening 110 in the first plate 110. As the second plate 104 approaches the first plate 102, the locking member 132 may pass through the notch 112 of the opening 110. The locking member 132 may flex or pivot to a first position as it passes through the notch 112. The locking member 132 may include a bias member that causes the locking member 132 to flex or pivot to a second position after passing through the notch 112. The lock screw 136 may further secure the locking member 132 within the notch 112 to keep the first plate 102 and second plate 104 rigidly fixed around the spinous processes 212 and 214.

The first plate 102 and the second plate 104 may include shaped regions to facilitate multilevel constructs including a plurality of devices 100. For example, both the first plate 102 and the second plate 104 may include an upper section 124, a middle section 126, and a lower section 128. The upper section 124 of each plate may include a first shaped region 142 and the lower section 128 of each plate may include a second shaped region 144. The first shaped region 142 may mate with the second shaped region 144 to form a chain of devices 100.

The first shaped region 142 may include a projection, taper, or convex portion and the second shaped region 144 may include a recess, cutout, or concave portion. The first and second shaped regions 142 and 144 may be reversed between upper and lower sections 124 and 128 as one skilled in the art would understand without affect on the multilevel capability of the device 100.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A system for surgically coupling a first spinous process with a second spinous process, comprising:
    a first plate with an opening extending from a first lateral surface to a first medial surface;
    a second plate with a pair of apertures extending from a second lateral surface to a second medial surface;
    a pair of guide members including flexible portions that attach to the first lateral surface of the first plate for inserting the first plate between the spinous processes and rigid elongate portions extending through the opening and received by the pair of apertures for guiding the second plate towards the first plate; and
    a coupler disposed between the pair of guide members that engages the opening to couple the first plate with the second plate.

2. The system of claim 1, further comprising a lock member that engages a notch of the opening.

3. The system of claim 1, further comprising a plurality of vertebral engagement features on the first and second medial surfaces.

4. The system of claim 1, further comprising a slot in the coupler for receiving bone-fusion material.

5. The system of claim 1, further comprising a set screw for locking the second plate to the first plate.

6. The system of claim 1, further comprising a tapered entry portion of the coupler for advancement through tissue and insertion into the opening.

7. The system of claim 1, wherein the guide members comprise one of rods, semi-flexible cables, semi-rigid cables, and living hinges.

8. The system of claim 1, further comprising a first shaped region on an upper section of the plates that mates with a second shaped region on a lower section of the plates.

9. The system of claim 1, further comprising:
    a third plate with a second opening extending from a third lateral surface to a third medial surface;
    a fourth plate with a second pair of apertures extending from a fourth lateral surface to a fourth medial surface;
    a second pair of guide members including flexible portions that attach to the third plate and elongate portions received by the second pair of apertures for guiding the fourth plate towards the third plate; and
    a second coupler disposed between the second pair of guide members that engages the second opening to couple the third plate with the fourth plate,
    wherein the first and second plates include a first shaped region on an upper section that mates with a second shaped region on a lower section of the third and fourth plates.

10. A method for surgically coupling spinous processes, comprising the steps of:
    inserting a first plate between a first and second spinous process and beneath a supraspinous ligament connecting the first and second spinous processes using a pair of guide members including flexible portions that attach to a first lateral surface of the first plate and rigid elongate portions that extend through an opening of the first plate;
    engaging the first plate with first lateral sides of the first and second spinous processes;
    sliding a second plate over the pair of guide members, the rigid elongate portions received by a pair of apertures for guiding the second plate towards the first plate;
    advancing the second plate to engage second lateral sides of the first and second spinous processes; and
    inserting a coupler through the opening of the first plate to rigidly couple the first and second plates.

11. The method of claim 10, further comprising attaching a pair of retention members on the pair of guide members on a lateral side of the second plate to maintain tension on the pair of guide members.

12. The method of claim 10, further comprising cutting a length from each of the guide members.

13. The method of claim 10, wherein the pair of guide members comprise one of rods, semi-flexible cables, semi-rigid cables, and living hinges.

* * * * *